(12) United States Patent
Kawakatsu et al.

(10) Patent No.: US 6,797,711 B2
(45) Date of Patent: Sep. 28, 2004

(54) BENZOFURAN DERIVATIVES AND PHARMACEUTICAL COMPOSITIONS CONTAINING THE SAME

(75) Inventors: Nobuyuki Kawakatsu, Kanagawa (JP); Takayuki Namiki, Kanagawa (JP); Norihisa Yamazaki, Kanagawa (JP); Masayuki Yuasa, Kanagawa (JP); Toyohiko Miki, Kanagawa (JP); Noriko Suenobu, Kanagawa (JP); Tomomasa Shimanuki, Kanagawa (JP)

(73) Assignee: Pola Chemical Industries, Inc., Shizuoka (JP)

( * ) Notice: Subject to any disclaimer, the term of this patent is extended or adjusted under 35 U.S.C. 154(b) by 0 days.

(21) Appl. No.: 10/450,842
(22) PCT Filed: Dec. 21, 2001
(86) PCT No.: PCT/JP01/11265
§ 371 (c)(1), (2), (4) Date: Jun. 26, 2003
(87) PCT Pub. No.: WO02/053550
PCT Pub. Date: Jul. 11, 2002

(65) Prior Publication Data
US 2004/0053940 A1 Mar. 18, 2004

(30) Foreign Application Priority Data
Dec. 27, 2000 (JP) ........................................ 2000-398075

(51) Int. Cl.[7] .................. A61K 31/495; C07D 403/00; A61P 37/00
(52) U.S. Cl. ................. 514/254.02; 544/374
(58) Field of Search ...................... 544/374; 514/254.02

(56) References Cited

FOREIGN PATENT DOCUMENTS

JP          11-116481          4/1999

*Primary Examiner*—Rita Desai
*Assistant Examiner*—Robert Shiao
(74) *Attorney, Agent, or Firm*—Oblon, Spivak, McClelland, Maier & Neustadt, P.C.

(57) ABSTRACT

Benzofuran derivatives represented by formula (I) or salts thereof:

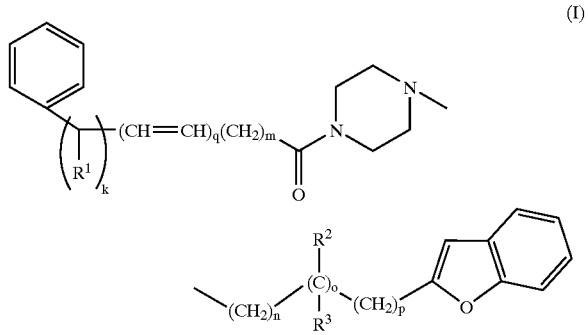

(wherein $R^1$ represents a phenyl group or a hydrogen atom; k is 0 or 1; each of m, n, o, p, and q is an integer of 0 to 5; and each of $R^2$ and $R^3$ represents a hydrogen atom or a hydroxyl group, or $R^2$ and $R^3$ together represent an oxygen atom, with proviso that k, q, and m, or n, o, and p are not simultaneously 0).

The compounds inhibit phosphorylation of STAT 6 and are useful in the treatment or prevention of allergic diseases.

14 Claims, No Drawings

BENZOFURAN DERIVATIVES AND PHARMACEUTICAL COMPOSITIONS CONTAINING THE SAME

TECHNICAL FIELD

The present invention relates to a benzofuran derivative possessing a JAK-STAT 6 phosphorylation inhibitory effect, and to a pharmaceutical composition containing the benzofuran derivative as an active ingredient.

BACKGROUND ART

Interleukin 4 is a cytokine involved in the onset and progress of inflammation, specifically known to be a factor leading to exacerbation of atopic dermatitis. Production of interleukin 4 is known to be accelerated by phosphorylation of STAT 6. This phenomenon is confirmed by the fact that interleukin 4 is blocked in STAT 6-knocked-out mice. Specifically, when phosphorylation of START 6 is suppressed by use of an agent, the reaction associated with such an interleukin 4 is inactivated effectively. On the basis of such findings, attention is paid particularly for the mechanism suppressing the inflammation caused by allergy through suppression of JAK-STAT 6, thus there has been strong demand for developing a means capable of inhibiting the phosphorylation of START 6.

Thus, an object of the present invention is to provide an STAT 6 phosphorylation inhibiting compound. Another object of the invention is to provide a pharmaceutical composition containing the compound useful for treating or preventing allergic disorders.

DISCLOSURE OF THE INVENTION

In view of the foregoing, the present inventors have carried out extensive studies in order to provide an STAT 6 phosphorylation inhibiting compound, and have found that benzofuran derivatives represented by the below-mentioned formula (I) and salts thereof exert an STAT 6 phosphorylation inhibitory effect. The present invention has been accomplished on the basis of this finding. Specifically, the present invention is directed to the following technical scopes described hereinbelow.

Accordingly, the present invention provides a benzofuran derivative represented by formula (I) or a salt thereof:

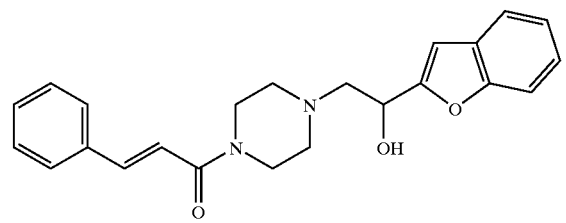

(wherein $R^1$ represents a phenyl group or a hydrogen atom; k is 0 or 1; each of m, n, o, p, and q is an integer of 0 to 5; and each of $R^2$ and $R^3$ represents a hydrogen atom or a hydroxyl group, or $R^2$ and $R^3$ together represent an oxygen atom, with proviso that k, q, and m, or n, o, and p are not simultaneously 0).

The present invention also provides a pharmaceutical composition and a JAK-STAT 6 phosphorylation inhibitor, the composition and inhibitor containing, as an active ingredient, a benzofuran derivative represented by formula (I) or a salt thereof.

The present invention also provides use of a benzofuran derivative represented by formula (I) or a salt thereof for producing a drug.

The present invention also provides a method for treating an allergic disorder characterized in that the method comprises administering, in an effective amount, a benzofuran derivative represented by formula (I) or a salt thereof.

BEST MODE FOR CARRYING OUT THE INVENTION

In formula (I), preferably, m is an integer of 0 to 3, n is an integer of 1 to 3, o is an integer of 0 or 1, p is an integer of 0 to 2, and q is an integer of 0 or 1.

Examples of preferred benzofuran derivatives falling within the scope of the present invention include the following compounds: 1-(2-(benzofuran-2-yl)-2-hydroxy)ethyl-4-cinnamoylpiperazine (Compound 1);

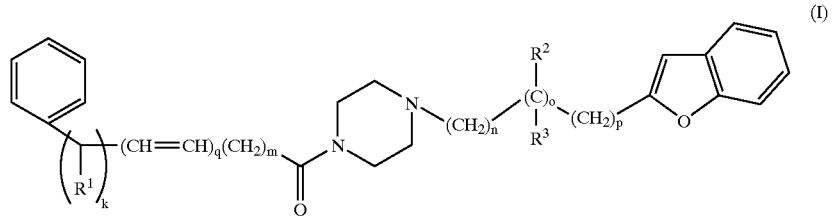

1-(2-(benzofuran-2-yl)-2-hydroxy)ethyl-4-(5,5-diphenylpentanoyl)piperazine (Compound 2);

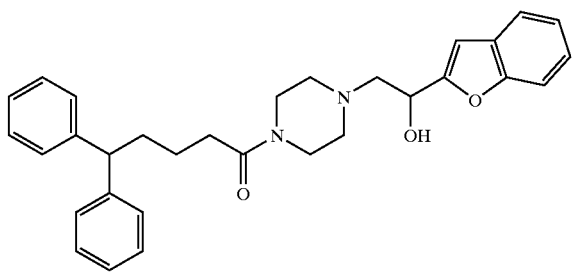

1-(2-(benzofuran-2-yl)-2-hydroxy)ethyl-4-(3,3-diphenylpropionyl)piperazine (Compound 3);

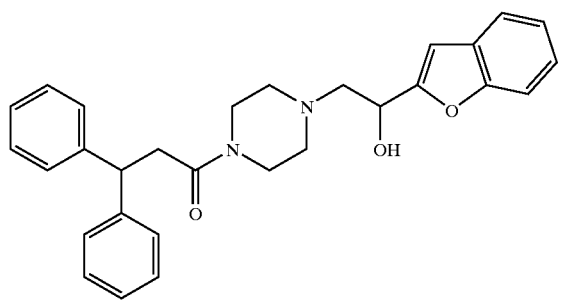

1-(benzofuran-2-yl)carbonyl-4-(3,3-diphenylpropionyl)piperazine (Compound 4);

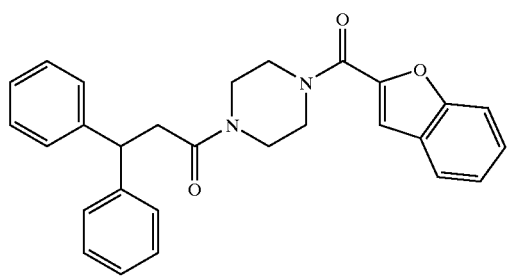

1-(benzofuran-2-yl)acetyl-4-(3,3-diphenylpropionyl)piperazine (Compound 5);

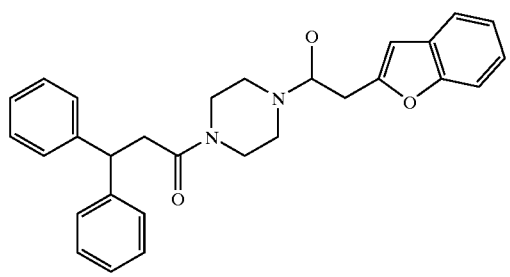

1-(benzofuran-2-yl)methyl-4-(3,3-diphenylpropionyl)piperazine (Compound 6); and

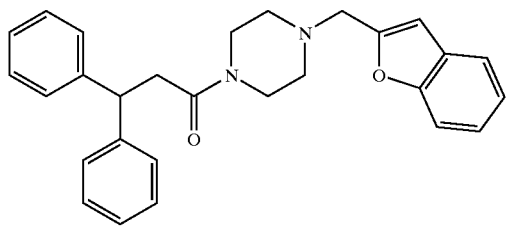

1-(2-(benzofuran-2-yl)ethyl)-4-(3,3-diphenylpropionyl)piperazine (Compound 7).

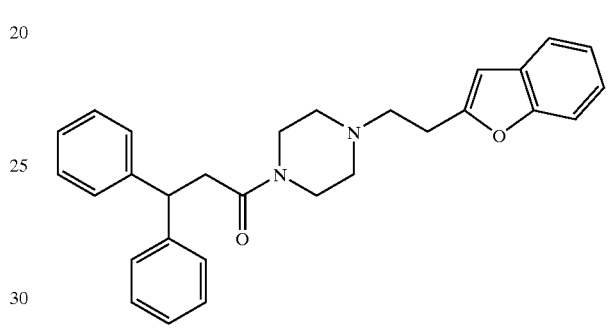

No particular limitation is imposed on the type of salts of the benzofuran derivative of the present invention, and any salts can be employed so long as the salts are physiologically acceptable. Examples of preferred salts include the corresponding salts of a mineral acid such as hydrochloric acid, sulfuric acid, nitric acid, or phosphoric acid; the corresponding salts of an organic acid such as citric acid, oxalic acid, or tartaric acid; and the corresponding salts of carbonic acid. Of these, the hydrochloric acid salts are particularly preferred from the viewpoint of excellent solubility and cost performance. Furthermore, the hydrochloric acid salts of Compounds 1 to 7 are more particularly preferred.

The benzofuran derivative (I) of the present invention can be produced in accordance with the following reaction scheme. Specifically, a (di)phenylalkyl(or alkenyl) carboxylic acid or a halide derived from the acid (II) is condensed with a protected piperazine (III) in which one nitrogen atom is protected by a protecting group (e.g., N-formylpiperazine), followed by deprotection, to thereby form an intermediate represented by formula (V). The intermediate (V) is reacted with a compound (VI) having a benzofuryl group and a leaving group such as a tosyl group or a halogen atom, to thereby yield the benzofuran derivative (I).

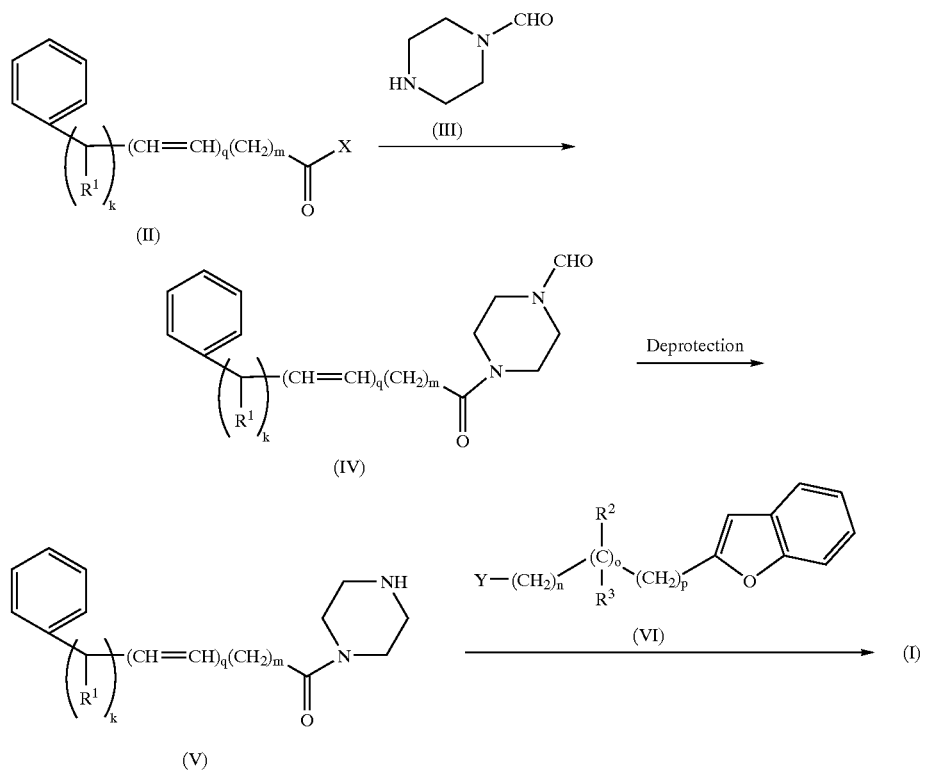

(wherein X represents a hydroxyl group or a halogen atom; Y represents a leaving group such as a tosyl group or a halogen atom; and $R^1$, $R^2$, $R^3$, k, m, n, o, p, and q have the same meanings as described above)

When the compound (II) is a carboxylic acid, the reaction with the piperazine compound (III) is preferably carried out in the presence of a peptide synthesis reagent such as diphenylphosphoryl azide, whereas when the compound (II) is a carboxylic acid halide, the reaction is preferably carried out in the presence of a base such as triethylamine or an alkali carbonate.

Deprotection of the compound (IV) can readily be performed by use of a hydrochloric acid-methanol mixture or a similar substance.

The reaction of the intermediate (V) and the benzofuran compound (VI) is preferably carried out in the presence of a base such as an alkali carbonate.

Through the above-described procedure, a compound represented by formula (I) in which $R^2$ and $R^3$ together represent an oxygen atom is obtained. By reducing the compound with a reducing agent such as sodium boron hydride, a compound represented by formula (I) in which one of $R^2$ and $R^3$ is a hydrogen atom and the other is a hydroxyl group can be obtained.

The thus-obtained benzofuran derivatives represented by formula (I) may be purified by means of recrystallization, column chromatography employing silica gel as a carrier, or similar means. The purified products may further be treated with acid, thereby forming the corresponding salts.

The benzofuran derivatives of the present invention represented by formula (I) and salts thereof exert a JAK-STAT 6 phosphorylation inhibitory effect. Thus, the derivatives and salts are useful as a drug for preventing or treating an allergic disorder of mammals (including human) and animals.

The pharmaceutical composition of the present invention is characterized by containing, as an active ingredient, one or more species selected from among benzofuran derivatives represented by formula (I) and salts thereof. Upon prevention or treatment of an allergic disorder, the benzofuran derivative of the present invention represented by formula (I) or a salt thereof is preferably administered in a daily dose per adult of 1 to 10,000 mg, singly or in a divided manner. Drug preparation is performed preferably in consideration of the dose. No particular limitation is imposed on the administration route of the benzofuran derivative of the present invention represented by formula (I) or a salt thereof, and all the species falling within the scope of the present invention can be administered in a stable form regardless of the administration route. Thus, the pharmaceutical composition of the present invention may be prepared into drug forms suitable for any administration routes. For example, the pharmaceutical composition is prepared in the forms of oil gels, emulsions, fine pills, granules, tablets, capsules, and liquids and solutions, and a further treatment such as coating is performed in accordance with needs. The products in the above forms can be administered through administration routes such as oral administration, intraveneous injection administration, intra-arterial injection administration, intrapylic injection administration, intraperitoneal injection administration, intrarectal administration (as a suppository), and skin external administration. In such drug preparation, any pharmacologically acceptable carriers which are generally employed in pharmaceutical compositions may be added to the aforementioned benzofuran derivative or a salt thereof. Examples of such carries include excipients, binders, disintegrants, coloring agents, sweetening and flavoring agents, dispersants, emulsifiers, stabilizers, pH regulators, isotonicity agents, and coating agents. The aforementioned benzofuran derivative represented by formula (I) or a salt thereof and any of the carriers are processed in a routine manner, to thereby produce the pharmaceutical composition of the present invention.

The thus-produced pharmaceutical composition of the present invention exerts the following effects: prevention of phosphorylation of JAK-STAT 6, blocking of interleukin 4, prevention and mitigation of exacerbation of allergic responses and inflammatory responses. No particular limitation is imposed on the disorders for which administration of the pharmaceutical composition of the present invention is suitable, so long as the disorders are allergic or inflammatory disorders relating to phosphorylation of JAK-STAT 6; i.e., interleukin 4 induced by the phosphorylation. Among these disorders, the pharmaceutical composition is particularly effective on atopic dermatitis. Examples of effects which are preferably exerted on such disorders by the pharmaceutical composition include amelioration and mitigation of the pathological conditions currently suffered by the patient and prevention of exacerbation of such conditions.

EXAMPLES

The present invention will next be described in more detail by way of examples, which should not be construed as limiting the invention thereto.

Example 1

1-(2-(benzofuran-2-yl)-2-hydroxy)ethyl-4-cinnamoylpiperazine (Compound 1)

Synthesis of Benzofuran-2-yl Bromomethyl Ketone

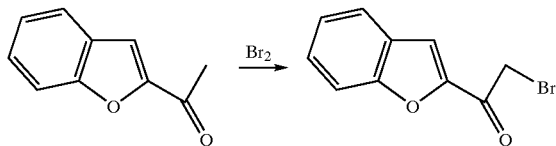

Benzofuran-2-yl methyl ketone (1.60 g, 10 mM) was dissolved in ether (20 mL). Under stirring of the mixture at room temperature, bromine (1.60 g) was added thereto. The resultant mixture was stirred for 10 minutes at room temperature, and poured in saturated sodium hydrogencarbonate solution, followed by extraction with ether (80 mL). The extract was washed with saturated brine and dried over magnesium sulfate, and the solvent was removed. Hexane was added to the residue and crystals were collected through filtration. The crystals were washed with hexane and dried, whereby 1.55 g of the product of interest was obtained (yield 69.4%).

NMR δ ppm(CDCl$_3$): 4.45(s, 2H), 7.35(m, 1H), 7.52(m, 1H), 7.60(d, 1H, J=8.4 Hz), 7.66(s, 1H), 7.74(d, 1H, J=7.8 Hz)

Synthesis of 1-cinnamoyl-4-formylpiperazine

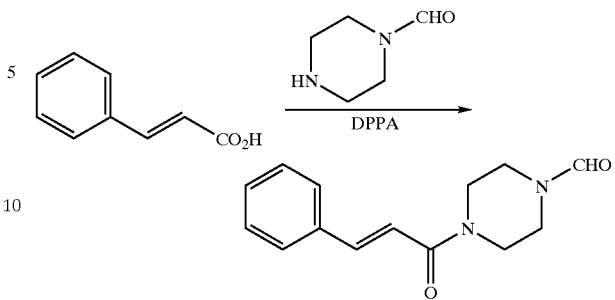

trans-Cinnamic acid (1.48 g) and N-formylpiperazine (2.28 g) were dissolved in N,N-dimethylformamide (20 mL), and the atmosphere was purged with nitrogen. While the solution was stirred in an ice-water bath, triethylamine (2.53 g) and diphenylphosphoryl azide (5.78 g) were added thereto, and stirring was continued for 1 hour and 45 minutes. The reaction mixture was poured in a mixture of ice and saturated sodium hydrogencarbonate solution, followed by extraction twice with ethyl acetate. The organic layers were combined and sequentially washed with 1N hydrochloric acid, saturated sodium hydrogencarbonate solution, and saturated brine, followed by drying over sodium sulfate anhydrate. The solvent was removed under reduced pressure, and the residue (colorless, oily) was purified through silica gel chromatography (silica gel 45 g, eluent; chloroform:methanol=200:1–100:1). The thus-purified product was dissolved in ethyl acetate, and the solution was sequentially washed with saturated sodium hydrogencarbonate solution and saturated brine, followed by drying over sodium sulfate anhydrate. The solvent was removed under reduced pressure, to thereby yield 1.22 g of the product of interest as a colorless oil (yield 50.0%).

NMR δ ppm(CDCl$_3$): 3.40–3.50(m, 2H), 3.55–3.85(m, 6H), 6.92(d, 1H, J=15.4 Hz), 7.30–7.45(m, 3H), 7.50–7.60 (m, 2H), 7.72(d, 1H, J=15.4 Hz), 8.13(s, 1H)

Synthesis of 1-cinnamoylpiperazine

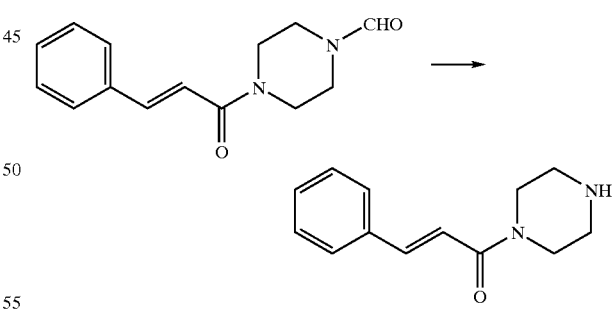

1-Cinnamoyl-4-formylpiperazine (1.22 g) was dissolved in chloroform (8 mL), and the atmosphere was purged with nitrogen. Under stirring of the solution in an ice-water bath, a liquid mixture (concentrated hydrochloric acid:methanol= 1:4) (5 mL) was added thereto. The mixture was stirred at room temperature for 20 hours and 30 minutes and in a 60° C.-water bath for one hour. Further, under stirring of the mixture in an ice-water bath, the same liquid mixture as described above (concentrated hydrochloric acid—methanol mixture) (4 mL) was added thereto, and the resultant mixture was stirred in a water bath for 6 hours at 60° C. The solvents were removed under reduced pressure, and water was added to the residue, followed by extraction with ethyl acetate. The ethyl acetate layer was removed, and pH of the water layer was adjusted to 8 to 9 with saturated sodium hydrogencarbonate solution, followed by extraction twice with chloroform. The chloroform layers were combined and dried over sodium sulfate anhydrate. The solvent was removed under reduced pressure, to thereby yield 1.14 g of the product of interest as a colorless oil. The product was employed in the next step in a crude form.

NMR δ ppm(CDCl$_3$): 2.91(t, 4H, J=5.0 Hz), 3.55–3.80 (brd, 4H), 6.93(d, 1H, J=15.4 Hz), 7.30–7.45(m, 3H), 7.50–7.60(m, 2H), 7.73(d, 1H, J=15.4 Hz)

Synthesis of 1-(2-(benzofuran-2-yl)-2-hydroxy)ethyl-4-cinnamoylpiperazine (Compound 1)

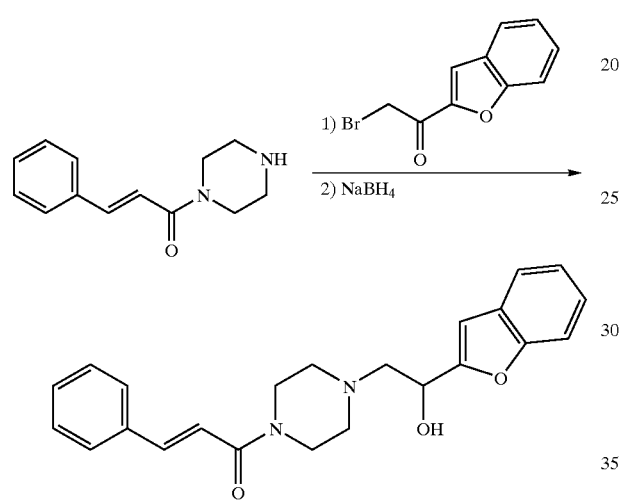

The piperazine compound (0.33 g, 1.5 mM) was dissolved in DMF (10 mL), and the above bromine compound (0.36 g) and potassium carbonate (0.21 g) were added thereto, followed by stirring at room temperature for two hours. The reaction mixture was poured in water, followed by extraction with benzene (120 mL). The extract was dried over magnesium sulfate, and the solvent was removed under reduced pressure, to thereby yield a ketone compound. The compound was dissolved in methanol (10 mL), and sodium boron hydride (57 mg) was added thereto, followed by stirring for 15 minutes. Sodium boron hydride (30 mg) was further added thereto, and the resultant mixture was stirred for 30 minutes. Subsequently, the reaction mixture was poured in saturated sodium hydrogencarbonate solution, followed by extraction with chloroform (120 mL). The extract was dried over magnesium sulfate, and the solvent was removed under reduced pressure. The residue was purified through silica gel column chromatography (silica gel 12 g, eluent; chloroform). The product was crystallized from hexane-chloroform. The thus-obtained crystals were separated through filtration, washed with hexane, and dried, to thereby yield 0.21 g of Compound 1 (yield 36.6%).

m.p. 126.5–128° C.

IR(KBr): 3420, 1646, 1602, 1455, 753

NMR δ ppm(CDCl$_3$): 2.57(m, 2H), 2.75(m, 2H), 2.80(dd, 1H, J=12.7, 3.5 Hz), 2.97(dd, 1H, J=12.7, 9.7 Hz), 3.67–3.90 (m, 4H), 4.95(dd, 1H, J=9.7, 3.5 Hz), 6.72(s, 1H), 6.89(d, 1H, J=15.7 Hz), 7.20–7.57(m, 9H), 7.68(d, 1H, J=15.7 Hz)

Example 2

1-(2-(benzofuran-2-yl)-2-hydroxy)ethyl-4-(5,5-diphenylpentanoyl)piperazine (Compound 2)

Synthesis of ethyl 5,5-diphenylpenta-2,4-dienoate

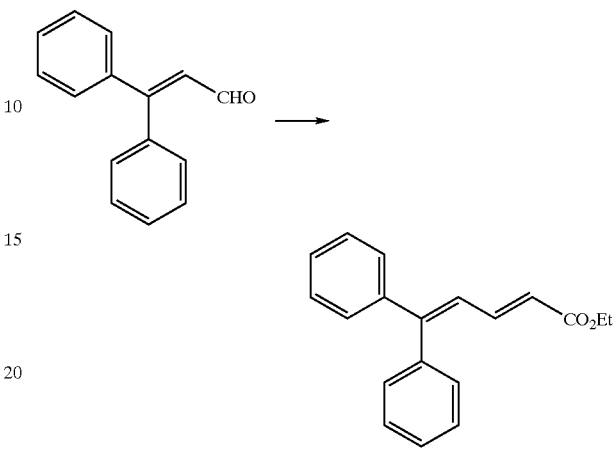

β-Phenylcinnamaldehyde (3.36 g), (carbethoxymethylene)triphenylphospholane (5.68 g), and benzoic acid (0.2 g) were added to anhydrous benzene (80 mL), and the mixture was refluxed under stirring for 3.5 hours. Subsequently, the resultant mixture was cooled to room temperature and condensed under reduced pressure. n-Hexane was added to the residue, and the insoluble matter was collected through filtration and washed several times with n-hexane. The filtrate and the resulting wash liquid were combined and condensed under reduced pressure. The product was purified through silica gel column chromatography (silica gel 40 g, eluent; n-hexane:ethyl acetate=50:1), to thereby yield 3.70 g of the product of interest (yield 82.4%).

NMR δ ppm(CDCl$_3$): 1.26(t, 3H, J=7.2 Hz), 4.17(q, 2H, J=7.2 Hz), 6.05(d, 1H, J=15.4 Hz), 6.79(d, 1H, J=11.9 Hz), 7.17–7.47(m, 11H)

Synthesis of 5,5-diphenylpenta-2,4-dienoic acid

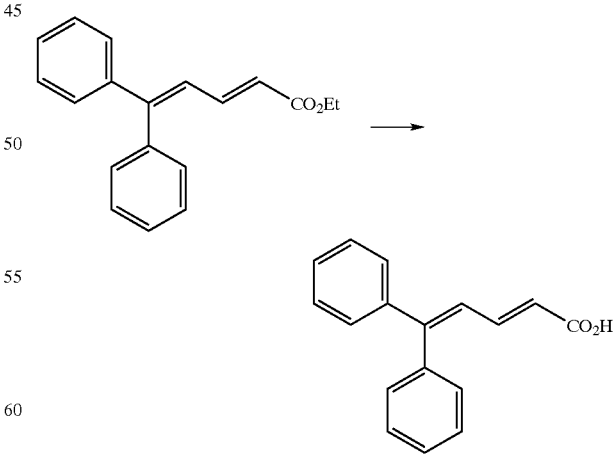

Ethyl 5,5-diphenylpenta-2,4-dienoate (3.70 g) was dissolved in ethanol (68 mL), and 1N sodium hydroxide solution (22 mL) was added thereto, followed by stirring at room temperature for 28.5 hours. Subsequently, while the mixture was stirred under ice-cooling, 1N hydrochloric acid was added thereto, and pH of the resultant mixture was adjusted to about 2. The mixture was condensed to a certain volume under reduced pressure. Water was added to the condensed product, and the thus-obtained solid was collected through filtration and washed several times with water, followed by air-drying, to thereby yield 3.16 g of the product of interest (yield 94.9%).

NMR δ ppm(CDCl$_3$): 6.03(d, 1H, J=14.9 Hz), 6.82(d, 1H, J=11.9 Hz), 7.13–7.52(m, 11H)

Synthesis of 5,5-diphenylpentanoic acid

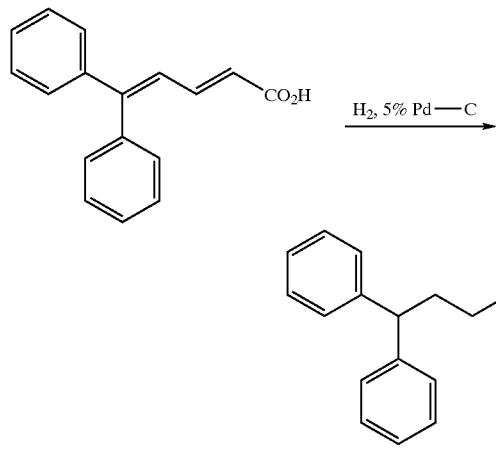

5,5-Diphenylpenta-2,4-dienoic acid (0.90 g) was dispersed in methanol (15 mL), and 5% palladium-carbon (90 mg) was added thereto. The mixture was subjected to catalytic reduction for two hours under hydrogen. The insoluble matter was separated through filtration and washed with methanol. The filtrate was subjected to distillation under reduced pressure, to thereby yield 0.89 g of the product of interest (yield 97.3%).

NMR δ ppm(CDCl$_3$): 1.53–1.67(m, 2H), 2.05–2.15(m, 2H), 2.37(t, 2H, J=7.6 Hz), 3.90(t, 1H, J=8.1 Hz), 7.12–7.32 (m, 10H)

Synthesis of 1-(5,5-diphenylpentanoyl)piperazine

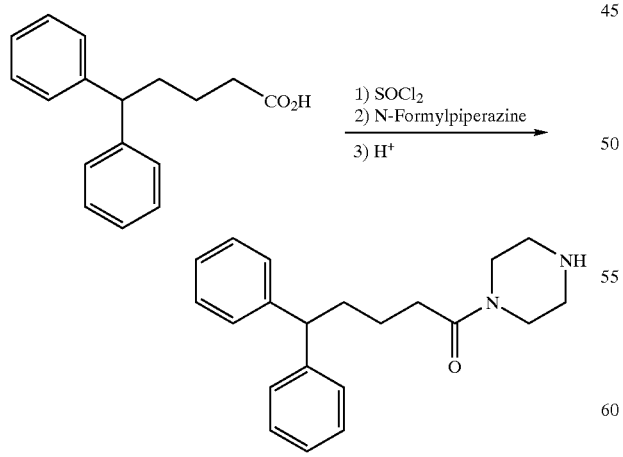

Thionyl chloride (14 mL) was added to 5,5-diphenylpentanoic acid (0.89 g), and the mixture was stirred for four hours at room temperature. The excessive reagent was removed under reduced pressure, to thereby yield an acid chloride. The acid chloride was dissolved in dichloromethane (10 mL). While the resultant mixture was stirred under cooling on ice, a solution of N-formylpiperazine (0.48 g) and triethylamine (0.43 g) in dichloromethane (4 mL) was added to the mixture at a time. Temperature of the mixture was elevated to room temperature, and the mixture was stirred for 30 minutes. Dichloromethane was removed under reduced pressure, and 1N hydrochloric acid was added thereto, followed by extraction with benzene (150 mL). The extract was washed with saturated sodium hydrogencarbonate solution and dried over magnesium sulfate, and the solvent was removed under reduced pressure, to thereby yield an acyl compound. The acyl compound was dissolved in a solvent mixture of chloroform (4.5 mL) and methanol (3.6 mL), and concentrated hydrochloric acid (0.9 mL) was added thereto, followed by stirring at room temperature for 20 hours. The solvent was removed under reduced pressure, and 1N hydrochloric acid was added to the residue, followed by washing with ether. The water layer was made alkaline by use of sodium hydroxide, followed by extraction with chloroform (150 mL). The extract was dried over magnesium sulfate, and the solvent was removed under reduced pressure, to thereby yield 0.77 g of the corresponding deformylated compound (yield 68.3%).

NMR δ ppm(CDCl$_3$): 1.58–1.65(m, 2H), 2.11(m, 2H), 2.32(t, 2H, J=7.6 Hz), 2.76(m, 4H), 3.31(t, 2H, J=5.4 Hz), 3.54(t, 2H, J=5.4 Hz), 3.91(t, 1H, J=8.1 Hz), 7.12–7.30(m, 10H)

Synthesis of 1-(2-(benzofuran-2-yl)-2-hydroxy)ethyl-4-(5,5-diphenylpentanoyl)piperazine (Compound 2) and a hydrochloric acid salt thereof

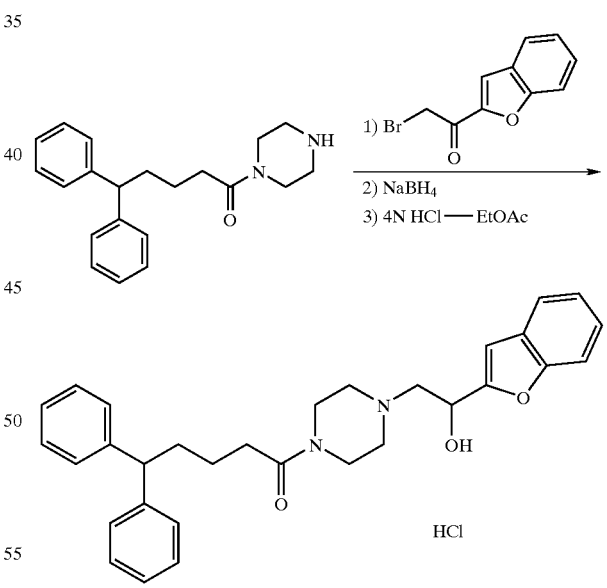

The procedure employed in the synthesis of the cinnamoyl compound was repeated, except that 5,5-diphenylpentanoylpiperazine was employed instead of cinnamoylpiperazine, to thereby yield Compound 2 (oil) (yield 89.6%).

The oil (0.55 g) was dissolved in ethyl acetate (5 mL), and under stirring of the mixture at room temperature, 4N hydrochloric acid-ethyl acetate solution (0.37 mL) was added thereto, followed by stirring for 15 minutes. Ether was added thereto, and the resultant mixture was stirred for 10 minutes. Thereafter, crystals were separated through filtration, washed with ether, and dried, to thereby yield 0.47 g of a hydrochloric acid salt of Compound 2 (yield 79.4%).

m.p. 178–180° C.

IR(KBr):3405, 3249, 1653, 1453, 751, 702

NMR δ ppm(CDCl$_3$): 1.58(m, 2H), 2.09(m, 2H), 2.28(bs, 2H), 2.68(m, 1H), 2.81(m, 1H), 3.40–4.05(m, 9H), 4.66(m, 1H), 5.68(m, 1H), 6.82(s, 1H), 7.13–7.31(m, 12H), 7.41(d, 1H, J=7.3 Hz), 7.54(d, 1H, J=7.0 Hz), 12.32(b, 1H)

Example 3

Synthesis of 1-(2-(benzofuran-2-yl)-2-hydroxy)ethyl-4-(3,3-diphenylpropionyl)piperazine (Compound 3)

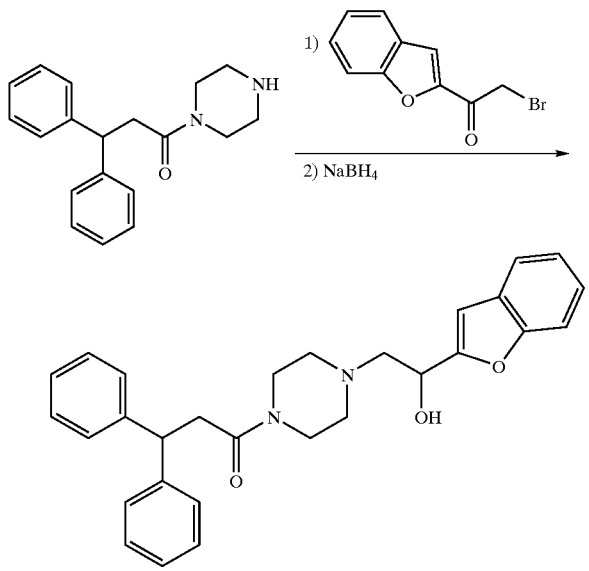

The procedure of Example 1 or 2 was repeated, except that 1-(3,3-diphenylpropionyl)piperazine synthesized in a manner similar to that of the synthesis of 1-cinnamoylpiperazine or that of 1-(5,5-diphenylpentanoyl)piperazine was employed, to thereby yield 0.48 g of Compound 3 (yield 70.6%).

m.p. 125.5–127.5° C.

IR(KBr):3400, 1643, 1628, 1618, 1454, 753, 700

NMR δ ppm(CDCl$_3$): 2.20(m, 1H), 2.30–2.40(m, 2H), 2.45–2.63(m, 1H), 2.65(dd, 1H, J=12.7, 3.5 Hz), 2.85(dd, 1H, J=12.7, 9.5 Hz), 3.05(d, 2H, J=7.3 Hz), 3.37(t, 2H, J=4.9 Hz), 3.50–3.85(m, 3H), 4.66(t, 1H, J=7.3 Hz), 4.87(dd, 1H, J=9.5, 3.5 Hz), 6.68(s, 1H), 7.14–7.32(m, 12H), 7.45(d, 1H, J=7.8 Hz), 7.54(dd, 1H, J=7.0, 1.9 Hz)

Example 4

Synthesis of 1-(benzofuran-2-yl)carbonyl-4-(3,3-diphenylpropionyl)piperazine (Compound 4)

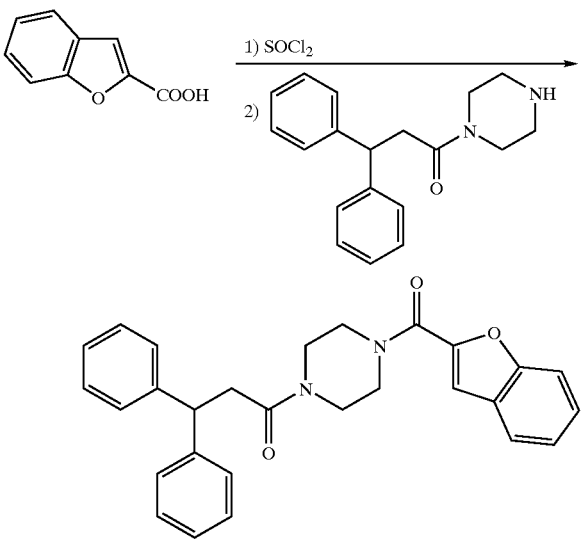

2-Benzofurancarboxylic acid (0.16 g) was dispersed in thionyl chloride (3 mL), and the mixture was refluxed for 1.5 hours. The mixture was cooled, and the excessive reagent was removed under reduced pressure. The residue was dissolved in dichloromethane (4 mL), and the piperazine compound (0.29 g) and triethylamine (0.12 g) was added thereto, followed by stirring for two hours at room temperature. The reaction mixture was diluted with chloroform (50 mL), and the resultant mixture was washed with 1N hydrochloric acid and saturated sodium hydrogencarbonate solution. The mixture was dried over magnesium sulfate, and the solvent was removed under reduced pressure. The residue was purified through silica gel column chromatography (silica gel (12 g), eluent; chloroform). The thus-purified product was crystallized from hexane-ethyl acetate, and the crystals were collected through filtration, washed with hexane, and dried. The thus-obtained crystals were recrystallized from hexane-ethyl acetate, to thereby yield 0.35 g of the target acyl compound (Compound 4) (yield 80.9%).

m.p. 130.5–132° C.

NMR δ ppm(CDCl$_3$): 3.11(d, 2H, J=7.8 Hz), 3.44(bs, 4H), 3.63–3.78(m, 4H), 4.68(t, 1H, J=7.8 Hz), 7.15–7.35(m, 12H), 7.41(t, 1H, J=8.1 Hz), 7.52(d, 1H, J=8.1 Hz), 7.66(d, 1H, J=8.1 Hz)

Example 5

1-(Benzofuran-2-yl)acetyl-4-(3,3-diphenylpropionyl)piperazine (Compound 5)

Synthesis of (benzofuran-2-yl)methanol

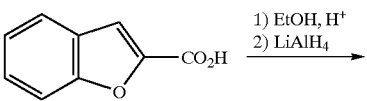

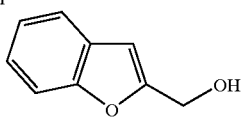

2-Benzofurancarboxylic acid (2.43 g) was dissolved in ethanol (50 mL), and concentrated sulfuric acid (1 mL) was added thereto, followed by refluxing for four hours. After cooling of the mixture, ethanol was removed under reduced pressure, saturated sodium hydrogencarbonate solution was added thereto, followed by extraction with ether (250 mL). The extract was dried over magnesium sulfate, and the solvent was removed under reduced pressure. The residue was purified through silica gel column chromatography (silica gel (30 g), eluent; hexane:ethyl acetate=5:1), to thereby yield 2.72 g of an ethyl ester (yield 95.4%).

The ethyl ester (2.72 g) was dissolved in THF (30 mL), and lithium aluminum hydride (0.54 g) was added thereto. The atmosphere was purged with nitrogen, the mixture was stirred for 30 minutes at room temperature. The reaction mixture was diluted with ether (100 mL), and saturated sodium sulfate solution was added thereto, to thereby decompose the excessive reagent. The organic layer was separated through decantation, and the residue was washed twice with ether (50 mL). The organic layers were combined and dried over magnesium sulfate, and the solvent was removed under reduced pressure. The residue was purified through silica gel column chromatography (silica gel (20 g), eluent; hexane:ethyl acetate=4:1), to thereby yield 1.95 g of the target alcohol compound (yield 92.0%).

NMR δ ppm(CDCl$_3$): 1.90(t, 1H, J=6.5 Hz), 4.78(d, 2H, J=6.5 Hz), 6.67(s, 1H), 7.18–7.32(m, 2H), 7.47(d, 1H, J=8.4 Hz), 7.55(dd, 1H, J=6.5, 1.1 Hz)

Synthesis of (benzofuran-2-yl)acetic acid

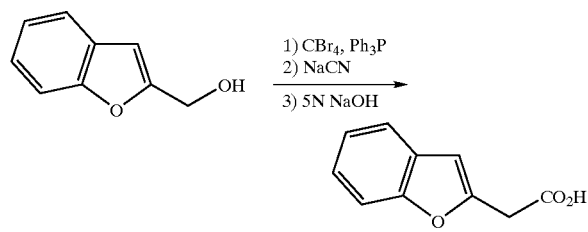

The alcohol compound (0.44 g) was dissolved in acetonitrile (8 mL), and triphenylphosphine (0.94 g) and carbon tetrabromide (1.19 g) were added thereto, followed by stirring for two hours at room temperature. The solvent was removed under reduced pressure, and ether (50 mL) was added to the residue, whereby the soluble matter contained in the residue was dissolved. The supernatant was separated through decantation, and the soluble matter contained in the residue was further extracted twice with ether (30 mL). The organic layers were combined and dried over magnesium sulfate, and the solvent was removed under reduced pressure. The residue was purified through silica gel column chromatography (silica gel (15 g), eluent; hexane:ethyl acetate=20:1), to thereby yield a bromine compound (0.64 g). The compound was disolved in DMSO (7 mL), and sodium cyanide (0.39 g) was added thereto, followed by stirring for one hour at room temperature. The reaction mixture was added to water, followed by extraction with ether (150 mL). The extract was washed with water and saturated brine and dried over magnesium sulfate, and the solvent was removed under reduced pressure. The residue was purified through silica gel column chromatography (silica gel (12 g), eluent; hexane:ethyl acetate=7:1), to thereby yield 0.20 g of a nitrile compound (yield 42.0%).

The nitrile compound (0.20 g) was dissolved in ethanol (2 mL), and 5N sodium hydroxide (2 mL) was added thereto, followed by refluxing for 5.5 hours. After cooling of the reaction mixture, water was added thereto, and the resultant mixture was washed with ether. The water layer was acidified with concentrated hydrochloric acid, followed by extraction with chloroform (50 mL and 10 mL). The organic layers were combined, washed with saturated brine, and dried over magnesium sulfate, and the solvent was removed under reduced pressure, to thereby yield 0.20 g of the target carboxylic acid (yield 89.2%).

NMR δ ppm(CDCl$_3$): 2.04(b, 1H), 3.89(s, 2H), 6.67(s, 1H), 7.16–7.32(m, 2H), 7.45(d, 1H, J=8.1 Hz), 7.53(d, 1H, J=8.1 Hz)

Synthesis of 1-(benzofuran-2-yl)acetyl-4-(3,3-diphenylpropionyl)piperazine (Compound 5)

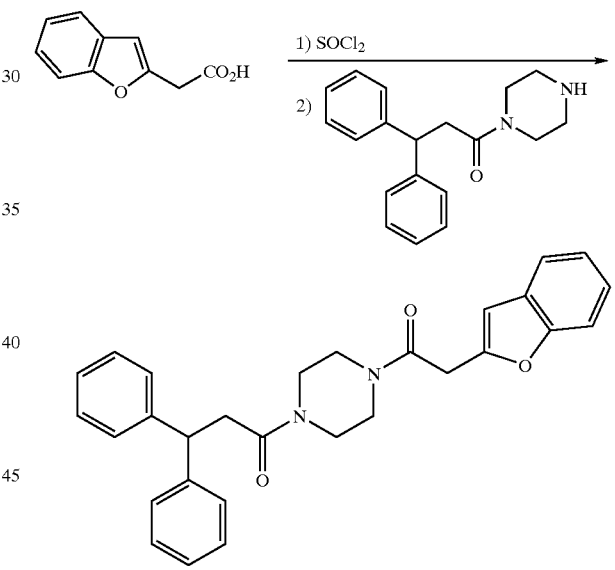

Thionyl chloride (1.5 mL) was added to the carboxylic acid (80 mg), and the mixture was stirred for 21 hours at room temperature. Subsequently, the excessive reagent was removed under reduced pressure. The residue was dissolved in dichloromethane (3 mL), and the piperazine compound (150 mg) and triethylamine (55 mg) were added thereto, followed by stirring for one hour at room temperature. The reaction mixture was diluted with chloroform (100 mL), and the diluted mixture was sequentially washed with 1N hydrochloric acid, saturated sodium hydrogencarbonate solution, and saturated brine and dried over magnesium sulfate. Thereafter, the solvent was removed under reduced pressure, and the residue was purified through silica gel column chromatography (silica gel (10 g), eluent; chloroform). The thus-purified product was crystallized from hexane-ethyl acetate, and the crystals were collected through filtration, washed with hexane, and dried, to thereby yield 155 mg of the target acyl compound (Compound 5) (yield 75.4%).

m.p. 162.5–164.5° C.

IR(KBr):3443, 1643, 1437, 1230, 1217, 744, 701

NMR δ ppm(CDCl$_3$): 4.01–3.13(m, 3H), 3.20–3.30(m, 1H), 3.30(s, 2H), 3.41–3.60(m, 4H), 3.86(m, 2H), 4.64(t, 1H, J=7.8 Hz), 6.57(s, 1H), 7.13–7.32(m, 12H), 7.42(d, 1H, J=7.8 Hz), 7.51(bd, 1H)

Example 6

Synthesis of 1-(benzofuran-2-yl)methyl-4-(3,3-diphenylpropionyl)piperazine (Compound 6)

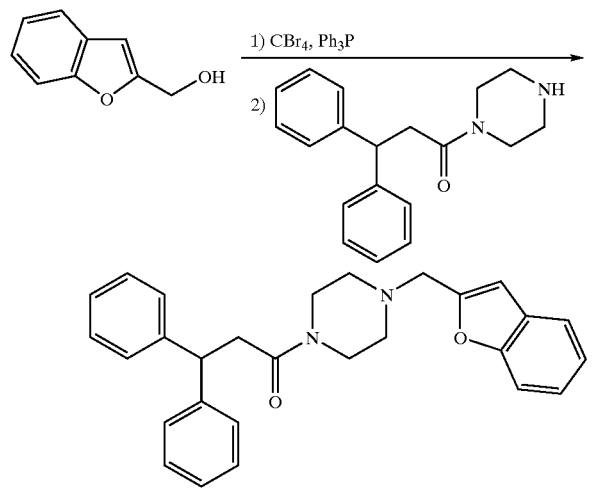

The bromine compound obtained from the alcohol compound (0.31 g) was dissolved in DMF (10 mL), the piperazine compound (0.74 g) and potassium carbonate (0.35 g) were added thereto, followed by stirring for one hour at room temperature. Ether (120 mL) was added to the reaction mixture, and the resultant mixture was washed twice with water. The mixture was dried over magnesium sulfate, and the solvent was removed under reduced pressure. The residue was purified through silica gel column chromatography (silica gel (15 g), eluent; chloroform). The thus-purified product was crystallized from hexane, and the crystals were collected through filtration, washed with hexane, and dried. The thus-obtained crystals were recrystallized from hexane-ethyl acetate, to thereby yield 0.53 g of the alkyl compound (Compound 6) (yield 60.7%).

m.p. 120.5–122° C.

IR(KBr):1617, 1456, 753, 709

NMR δ ppm(CDCl$_3$): 2.21(t, 2H, J=4.9 Hz), 2.40(t, 2H, J=4.9 Hz)3.03(d, 2H, J=7.6 Hz), 3.37(t, 2H, J=4.9 Hz), 3.60(t, 2H, J=4.9 Hz), 3.63(s, 2H), 4.64(t, 1H, J=7.6 Hz), 6.57(s, 1H), 7.10–7.30(m, 12H), 7.47(d, 1H, J=8.1 Hz), 7.53(d, 1H, J=8.1 Hz)

Example 7

1-(2-(Benzofuran-2-yl)ethyl)-4-(3,3-diphenylpropionyl)piperazine (Compound 7)

Synthesis of 2-(benzofuran-2-yl)ethyl tosylate

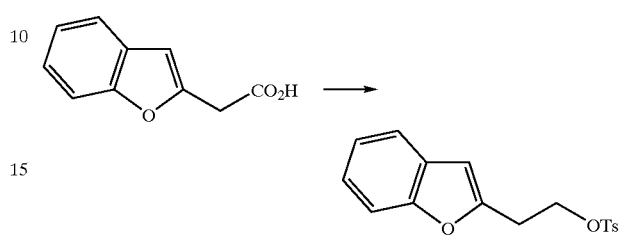

The carboxylic acid (0.35 g) was dissolved in ethanol (5 mL), and concentrated sulfuric acid (0.3 mL) was added thereto, followed by refluxing for three hours. After cooling of the mixture, ethanol was evaporated to thereby condense the mixture, and ether (200 mL) was added to the residue. The mixture was sequentially washed with saturated sodium hydrogencarbonate and saturated brine and dried over magnesium sulfate. The solvent was removed under reduced pressure, and the residue was dissolved in THF (6 mL). Lithium aluminum hydride (0.1 g) was added to the soluion, and the atmosphere was purged with nitrogen, followed by stirring for 13 hours. The reaction mixture was diluted with ether (50 mL), and saturated sodium sulfate was added thereto, whereby the excessive reagent was decomposed. The supernatant was separated through decantation, and the residue was washed twice with ether (20 mL). The resulting wash liquid and the supernatant were combined and dried over magnesium sulfate, and the solvent was removed under reduced pressure. The residue was purified through silica gel column chromatography (silica gel (12 g), eluent; hexane-:ethyl acetate=3:1), to thereby yield 0.25 g of an alcohol compound (yield 76.8%).

The alcohol compound was dissolved in dichloromethane (5 mL), and p-toluenesulfonyl chloride (0.37 g) and triethylamine (0.28 mL) were added thereto, followed by stirring for 1.75 hours at room temperature. p-Toluenesulfonyl chloride (0.1 g) and triethylamine (0.08 mL) were added thereto, and the mixture was stirred for a further four hours. The reaction mixture was diluted with chloroform (70 mL), and the diluted mixture was sequentially washed with 1N hydrochloric acid, saturated sodium hydrogencarbonate, and saturated brine and dried over magnesium sulfate. Thereafter, the solvent was removed under reduced pressure, and the residue was purified through silica gel column chromatography (silica gel (12 g), eluent; hexane:ethyl acetate=7:1), to thereby yield 0.47 g of the product of interest (yield 96.4%).

NMR δ ppm(CDCl$_3$): 2.37(s, 3H), 3.13(t, 2H, J=6.5 Hz), 4.36(t, 2H, J=6.5 Hz), 6.43(s, 1H), 7.16–7.34(m, 5H), 7.46 (m, 1H), 7.68(d, 2H, J=8.4 Hz)

Synthesis of 1-(2-(benzofuran-2-yl)ethyl)-4-(3,3-diphenylpropionyl)piperazine (Compound 7)

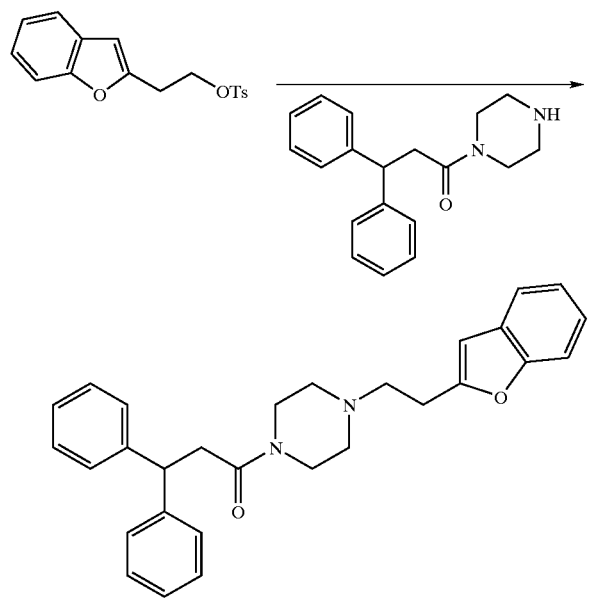

The tosylate compound (0.45 g) and the piperazine compound (0.42 g) were dissolved in DMF (10 mL), and potassium carbonate (0.21 g) was added thereto, followed by stirring for two hours in an oil bath at 100° C. The reaction mixture was added to water, and the mixture was subjected to extraction with ether (120 mL). The ether layer was washed with water and saturated brine and dried over magnesium sulfate. The solvent was removed under reduced pressure, and the residue was purified through silica gel column chromatography (silica gel (12 g), eluent; chloroform). The thus-purified product was crystallized from hexane and recrystallized from hexane-ethyl acetate, to thereby yield 0.29 g of Compound 7 (yield 46.4%).

m.p. 123.3–124.1° C.

IR(KBr):1636, 1453, 1253, 749, 702

NMR δ ppm(CDCl$_3$): 3.20(t, 2H, J=4.9 Hz), 2.37(t, 2H, J=4.9 Hz), 2.70(t, 2H, J=7.6 Hz), 2.92(t, 2H, J=7.6 Hz), 3.05(d, 2H, J=7.3 Hz), 3.35(t, 2H, J=4.9 Hz), 3.57(t, 2H, J=4.9 Hz), 4.66(t, 1H, J=7.3 Hz), 6.41(s, 1H), 7.13–7.51(m, 14H)

Example 8

JAK-STAT 6 Phosphorylation Inhibitory Effect

JAK-STAT 6 phosphorylation inhibitory effect of Compounds 1 to 7 (Compound 2 was employed in the form of a hydrochloric acid salt) were measured through immunoblotting as described below.

Preparation of samples: The measurement was performed by use of U937 cells which had been cultured for two to three days in a 75-cm$^3$ flask. RPMI 1640 (10% FBS) was employed as a medium. By use of the medium, a cell suspension (1.0×10$^6$ cells/mL) was prepared. The cell suspension was dispensed to 1.5-mL test tubes (1 mL/tube each), and the sample compounds (10 μL each) were individually added to the above test tubes, followed by incubation for 30 minutes at 37° C.

Each mixture was centrifuged at 15,000 rpm for 20 seconds at 4° C., and the supernatant was removed by use of an aspirator. Lysis buffer (100 μL) was added thereto, and the resultant mixture was stirred thoroughly.

The mixture was processed for five minutes at 95° C. and centrifuged at 15,000 rpm for 20 seconds at 4° C., to thereby prepare a sample.

Measurement: The thus-prepared sample was electrophoresed by use of a gel (ATTO AE-6000 (PAGEL; NPU-7.5L)), and sandwich antigen-antibody reaction was performed by use of anti-phosphorylized-STAT 6 antibody (Phospho-STAT 6 (Tyr641) Antibody) serving as a primary antibody and anti-rabbit antibody and anti-biotin antibody serving as secondary antibodies. Phosphorylation inhibitory effect of the sample was determined on the basis of the luminescence intensity of the blots.

The results are shown in Table 1. As is apparent from the results, the benzofuran derivatives of the present invention represented by formula (I) and salts thereof were found to exhibit JAK-STAT 6 phosphorylation inhibitory effect.

TABLE 1

| Sample | JAK-STAT 6 phosphorylation inhibitory effect |
|---|---|
| Compound 1 | 93.4 |
| Compound 2 (hydrochloric acid salt) | 52.8 |
| Compound 3 | 68.6 |
| Compound 4 | 63.0 |
| Compound 5 | 35.7 |
| Compound 6 | 39.8 |
| Compound 7 | 71.4 |

Example 9

CD23 Expression Inhibitory Effect

CD23 Expression inhibitory effect was measured by use of U937 cells as employed in Example 8 through flow cytometry. FITC Anti-Human CD23 was employed as an antibody. The results are shown in Table 2. As is apparent from the results, the benzofuran derivatives of the present invention were found to exhibit excellent CD23 expression inhibitory effect.

TABLE 2

| Sample | CD23 expression inhibitory effect |
|---|---|
| Compound 1 | 72.2 |
| Compound 2 (hydrochloric acid salt) | 45.1 |
| Compound 3 | 54.2 |
| Compound 4 | 67.2 |
| Compound 5 | 35.7 |
| Compound 6 | 49.5 |
| Compound 7 | 49.0 |

Example 10

According to the below-described formulation, a pharmaceutical composition for treating an allergic disorder falling within the scope of the present invention was prepared. Specifically, the components were fed in a fluidized bed granular and thoroughly mixed. Thereafter, the mixture was granulated in the fluidized bed, while water (20 parts by weight) was sprayed to the mixture. The thus-obtained granules were filtered, and 100-pass-200-on granules were collected, whereby the pharmaceutical composition of the present invention was obtained in the form of granules.

| | |
|---|---|
| Lactose | 30 parts by weight |
| Crystalline cellulose | 30 parts by weight |
| Starch | 19 parts by weight |
| Hydrochloric acid salt of Compound 2 | 15 parts by weight |
| Hydroxypropyl cellulose | 5 parts by weight |
| Magnesium stearate | 1 part by weight |

Industrial Applicability

The present invention can provide a pharmaceutical composition which inhibits phosphorylation of STAT 6 and is useful for treatment and prevention of allergic disorders.

What is claimed is:

1. A benzofuran represented by formula (I) or a salt thereof:

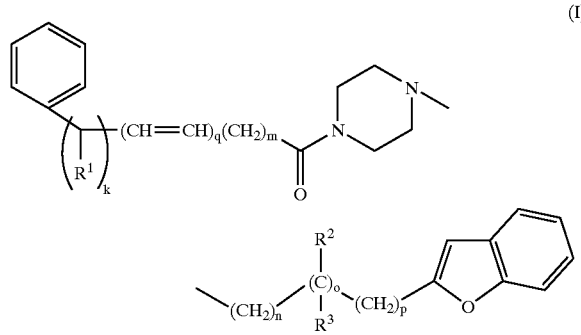

wherein
$R^1$ represents a phenyl group or a hydrogen atom;
k is 0 or 1;
each of m, n, o, p, and q is an integer of 0 to 5; and
each of $R^2$ and $R^3$ represents a hydrogen atom or a hydroxyl group, or $R^2$ and $R^3$ together represent an oxygen atom,
with proviso that k, q, and m, or n, o, and p are not simultaneously 0.

2. A benzofuran or a salt thereof as described in claim 1, wherein the benzofuran derivative represented by formula (I) is 1-(2-(benzofuran-2-yl)-2-hydroxy)ethyl-4-cinnamoylpiperazine, 1-(2-(benzofuran-2-yl)-2-hydroxy)ethyl-4-(5,5-diphenylpentanoyl)piperazine, 1-(2-(benzofuran-2-yl)-2-hydroxy)ethyl-4-(3,3-diphenylpropionyl)piperazine, 1-(benzofuran-2-yl)carbonyl-4-(3,3-diphenylpropionyl)piperazine, 1-(benzofuran-2-yl)acetyl-4-(3,3-diphenylpropionyl)piperazine, 1-(benzofuran-2-yl)methyl-4-(3,3-diphenylpropionyl)piperazine, or 1-(2-(benzofuran-2-yl)ethyl)-4-(3,3-diphenylpropionyl)piperazine.

3. A benzofuran or a salt thereof as described in claim 1, wherein
m is an integer of 0 to 3;
n is an integer of 1 to 3;
o is an integer of 0 or 1;
p is an integer of 0 to 2; and
q is an integer of 0 or 1.

4. A pharmaceutical composition comprising, a benzofuran or a salt thereof as described in claim 1 and a pharmacologically acceptable carrier.

5. A method of treating an allergic disorder, comprising administering an effective amount to of the benzofuran as described in claim 1 or a salt thereof to a subject.

6. The method of claim 5, wherein the benzofuran is 1-(2-(benzofuran-2-yl)-2-hydroxy)ethyl-4-cinnamoylpiperazine, 1-2-(benzofuran-2-yl)-2-hydroxy)ethyl-4-(5,5-diphenylpentanoyl)piperazine, 1-(2-(benzofuran-2-yl)-2-hydroxy)ethyl-4-(3,3-diphenylpropionyl)piperazine, 1-(berizofuran-2-yl)carbonyl-4-(3,3-diphenylpropionyl)piperazine, 1-(benzofuran-2-yl)acetyl-4-(3,3-diphenylpropionyl)piperazine, 1-(benzofuran-2-yl)methyl-4-(3,3-diphenylpropionyl)piperazine, or 1-(2-(benzofuran-2-yl)ethyl)-4-(3,3-diphenylpropionyl)piperazine.

7. The method of claim 5, wherein
m is an integer of 0 to 3;
n is an integer of 1 to 3;
o is an integer of 0 or 1;
p is an integer of 0 to 2; and
q is an integer of 0 or 1.

8. The method of claim 5, wherein the subject is a human.

9. The method of claim 5, wherein the subject is a non-human animal.

10. A method of treating atopic dermatitis, comprising administering an effective amount to of the benzofuran as described in claim 1 or a salt thereof to a subject.

11. The method of claim 10, wherein the benzofuran is 1-(2-(benzofuran-2-yl)-2-hydroxy)ethyl-4-cinnamoylpiperazine, 1-2-(benzofuran-2-yl)-2-hydroxy)ethyl-4-(5,5-diphenylpentanoyl)piperazine, 1-(2-(benzofuran-2-yl)-2-hydroxy)ethyl-4-(3,3-diphenylpropionyl)piperazine, 1-(benzofuran-2-yl)carbonyl-4-(3,3-diphenylpropionyl)piperazine, 1-(benzofuran-2-yl)acetyl-4-(3,3-diphenylpropionyl)piperazine, 1-(benzofuran-2-yl)methyl-4-(3,3-diphenylpropionyl)piperazine, or 1-(2-(benzofuran-2-yl)ethyl)-4-(3,3-diphenylpropionyl)piperazine.

12. The method of claim 10, wherein
m is an integer of 0 to 3;
n is an integer of 1 to 3;
o is an integer of 0 or 1;
p is an integer of 0 to 2; and
q is an integer of 0 or 1.

13. The method of claim 10, wherein the subject is a human.

14. The method of claim 10, wherein the subject is a non-human animal.

* * * * *

UNITED STATES PATENT AND TRADEMARK OFFICE
CERTIFICATE OF CORRECTION

PATENT NO. : 6,797,711 B2
DATED : September 29, 2004
INVENTOR(S) : Nobuyuki Kawakatsu et al.

It is certified that error appears in the above-identified patent and that said Letters Patent is hereby corrected as shown below:

<u>Column 22,</u>
Line 23, "1-berizofuran-2-yl)" should read -- 1-benzofuran-2-yl) --
Line 40, "amount to of the benzofuran" should read -- amount of the benzofuran --.

Signed and Sealed this

Eighth Day of February, 2005

JON W. DUDAS
*Director of the United States Patent and Trademark Office*